(12) United States Patent (10) Patent No.: US 7,876,882 B2
Meyer et al. (45) Date of Patent: Jan. 25, 2011

(54) AUTOMATED SOFTWARE SYSTEM FOR BEAM ANGLE SELECTION IN TELETHERAPY

(75) Inventors: Robert R. Meyer, Madison, WI (US); Leyuan Shi, Madison, WI (US); Warren D. D'Souza, Baltimore, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 245 days.

(21) Appl. No.: 12/025,588

(22) Filed: Feb. 4, 2008

(65) Prior Publication Data

US 2008/0310590 A1 Dec. 18, 2008

Related U.S. Application Data

(60) Provisional application No. 60/888,013, filed on Feb. 2, 2007.

(51) Int. Cl.
*A61N 5/10* (2006.01)

(52) U.S. Cl. ......................................................... 378/65

(58) Field of Classification Search ................... 378/65
See application file for complete search history.

(56) References Cited

U.S. PATENT DOCUMENTS

2003/0138077 A1 * 7/2003 Lee .............................. 378/65

2004/0264640 A1 * 12/2004 Myles ............................ 378/65

OTHER PUBLICATIONS

Zhang et al., "A Framework for Combining Beam Angle Selection and Dose Optimization in Intensity-Modulated Radiation Therapy", (Nov. 30, 2006), pp. 1-28.*

D'Souza, W. D. et al., "Selection of beam orientations in intensity-modulated radiation therapy using single-beam indices and integer programming," Phys. Med. Biol. 49 (2004) 3465-3481, IOP Publ. Ltd., UK.

Shi, L. et al., "Using Nested Partitions for beam Angle Selection in Intensity-Modulated Radiation Therapy," Proceeding of 2006 NSF Design, Service and Mfg Grantees and Res. Conf., St Louis, MO Grant #0400294, 0355567.

* cited by examiner

*Primary Examiner*—Chih-Cheng G Kao
(74) *Attorney, Agent, or Firm*—Michael Best & Friedrich LLP; Jonathan M. Fritz

(57) ABSTRACT

A novel approach to generating radiation treatment plans through a nested partitions framework provides an optimization of radiation delivery. The nested partitions approach couples beam angle selection and dose optimization to solve treatment planning problems. An optimal beam angle selection is provided to best treat tumors, while minimizing exposure to the surrounding healthy tissues.

26 Claims, 5 Drawing Sheets

AUTOMATED SOFTWARE SYSTEM FOR BEAM ANGLE SELECTION IN TELETHERAPY

CROSS REFERENCE TO RELATED APPLICATIONS

The present application claims priority to U.S. Provisional Patent Application Ser. No. 60/888,013, filed Feb. 2, 2007, which is fully incorporated herein by reference.

STATEMENT REGARDING FEDERALLY SPONSORED RESEARCH OR DEVELOPMENT

The invention was made with United States Government support awarded by the following agency: National Science Foundation (NSF) under Grant #DMI-0400294 and Grant # 03-65557.

The present invention relates to systems and methods for generating patient specific radiation treatment plans. More particularly the present invention relates to the optimization of radiation treatment plans for cancer patients.

BACKGROUND OF THE INVENTION

Health care represents the largest industry in the United States, current estimates place it at approximately 16% of the gross domestic product, and increasing. Technological innovations over the last half century have aided the growth of the health care industry. Health care systems engineering is a particular catalytic area of development within the health care industry. Industrial and systems engineers along with operations researchers are making significant advances in the application of health care delivery optimization approaches. One specific and promising subset of health care delivery includes cancer treatment planning, specifically radiation treatment planning (RTP) for the treatment of cancer.

Radiotherapy treatment planning has been revolutionized through the use of CT and MRI scanners, which provide three-dimensional delineation of tumors and adjacent healthy tissues. Tumor treatment simulation techniques have enhanced the accuracy of radiotherapy treatment. 3D Conformal Radiotherapy (3DCRT) enables the radiation beam to be shaped to fit the target profile from a beam's eye view (BEV). A variable number of beams is often used for 3DCRT. Higher effective doses of radiation can therefore be delivered to the target tissue, while limiting the exposure to healthy tissue adjacent to the target. 3DCRT techniques have undergone technological advancement to provide advanced high precision radiation. Intensity-Modulated Radiation Therapy (IMRT) is often considered the next generation of 3DCRT, providing targeted radiation delivery to tumors by controlling or modulating the radiation beam's intensity. IMRT often allows for a higher dose of radiation as compared to previously known methods. However, IMRT is a complex technology for radiation treatment, which often involves the use of a multileaf collimator to shape the beam and makes it possible to control, or modulate, the amount of radiation that is delivered from each of the delivery directions relative to the patient. Due to the complexity there are numerous treatment planning problems, which include radiation dose optimization and beam angle selection.

Current commercial treatment planning systems for radiation therapy often require the user to employ expert judgment to determine the beam angles that are required to use those systems. An expert's judgment is often subject to interpretation and a host of variables that may lead to inaccurate results.

It would be advantageous for a treatment planning system for radiation therapy to generate beam sets that demonstrate significant improvements relative to beam sets that are obtained through expert judgment. It would be further advantageous to couple beam angle optimization with dose optimization. It would be a further advantage to automate the coupling of beam angle optimization and dose optimization for RTP.

BRIEF DESCRIPTION OF THE INVENTION

In accordance with at least one embodiment of the present invention, a medical treatment planning system is provided. The system includes a central processing unit (CPU) for performing computer executable instructions and a memory storage device for storing computer executable instructions that when executed by the CPU cause the CPU to perform a process for generating a radiation treatment plan through a nested partitioning framework.

In accordance with an alternative embodiment of the present invention, a method of preparing a patient treatment plan is provided. The method includes obtaining medical patient imaging data, identifying a target tissue within the patient based in part on the imaging data and generating a treatment plan based in-part on a nested partition framework. The imaging data is used within the nested partition framework.

In accordance with yet another alternative embodiment of the present invention, a medical treatment planning system is provided. The system includes a processor for performing computer executable instructions and a memory device for storing computer executable instructions. When the instructions are executed by the processor, a process for generating a radiation treatment plan is performed. Additionally, the process performs an algorithmic coupling of beam angle selection and dose optimization within a nested partitioning framework.

DETAILED DESCRIPTION

Various embodiments of the present invention incorporate nested partitioning (NP) for solving a variety of treatment planning problems. One such problem is optimal beam angle selection, which can be generated for more effectively treating tumors and sparing the surrounding healthy tissues based upon data analysis steps including nested partitioning. In at least one embodiment of the invention this is an iterative process using parallel computing power or shared processors. In at least one embodiment of the invention a method for identifying tumor tissue includes an input generation step, an initialization phase, and a selection phase. Various embodiments of the present invention employ radiotherapy treatments for specific types of cancers including, but not limited to, prostate cancer, primary brain tumors, metastatic brain tumors, head and neck cancers, and other select cancers.

Method of Generating RTP

Figure 1:
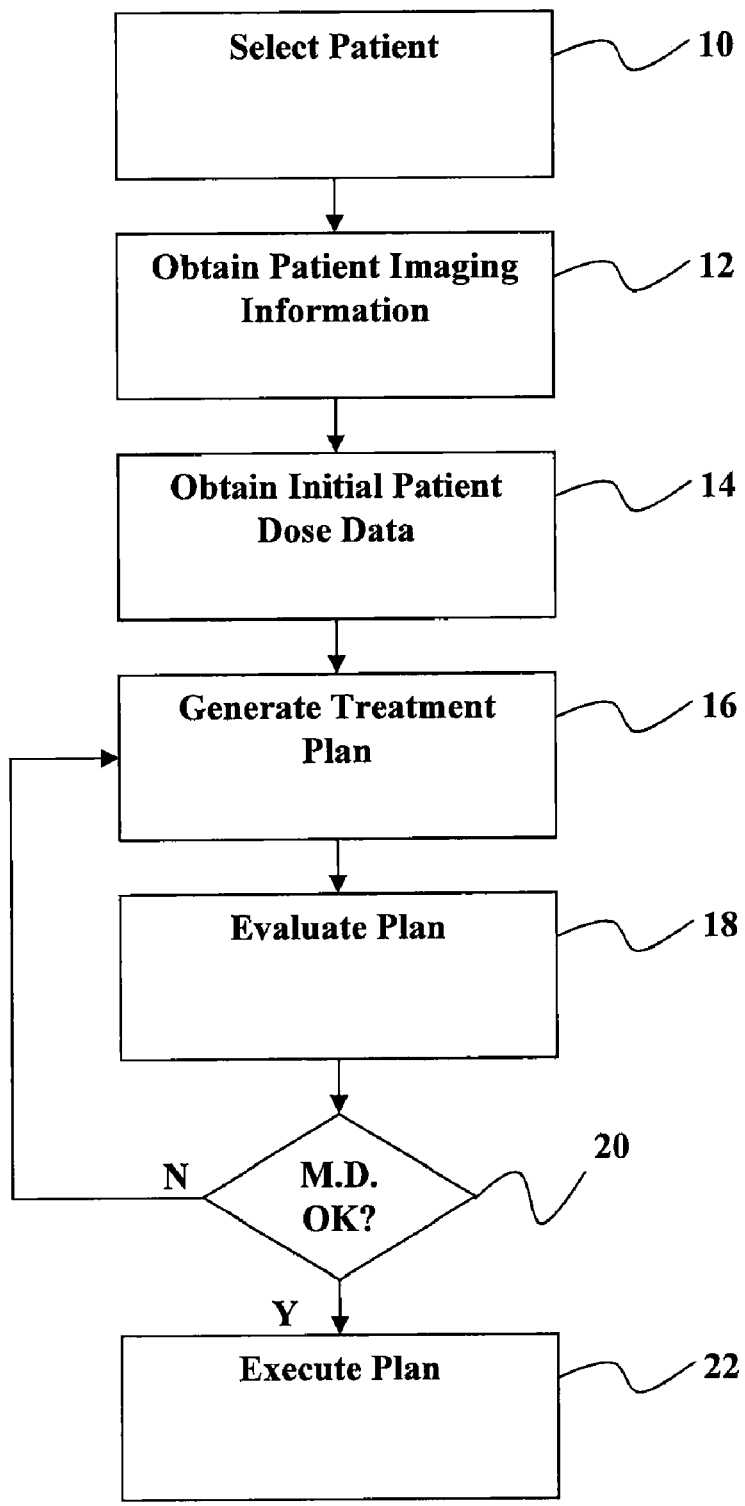
FIG. 1 is a flow chart representing the generation and execution of a radiation treatment plan in accordance with at least one embodiment of the present invention.

Referring to FIG. 1, a novel method for generating a radiotherapy treatment plan (RTP) is provided. An RTP is developed for each cancer patient for the purpose of most effectively treating the patient's cancer. The patient is selected at step 10 and patient imaging information is obtained at step 12. The patient imaging information can be selected from a variety of known methods, including CT, MRI, PET, x-rays, photon therapy data and charged particle data. Alternatively, imaging information can be obtained from additional planar or volumetric imaging modalities. Initial radiotherapy dose information is obtained at step 14 for the patient. The imaging data and the initial dose data are combined at step 16 to generate a radiotherapy treatment plan. The RTP is evaluated at step 18, if the plan is acceptable to the patient's physician at step 20, then the plan is executed at step 22. If the plan is not acceptable to the physician, then the sequence reverts to step 16.

Figure 2:
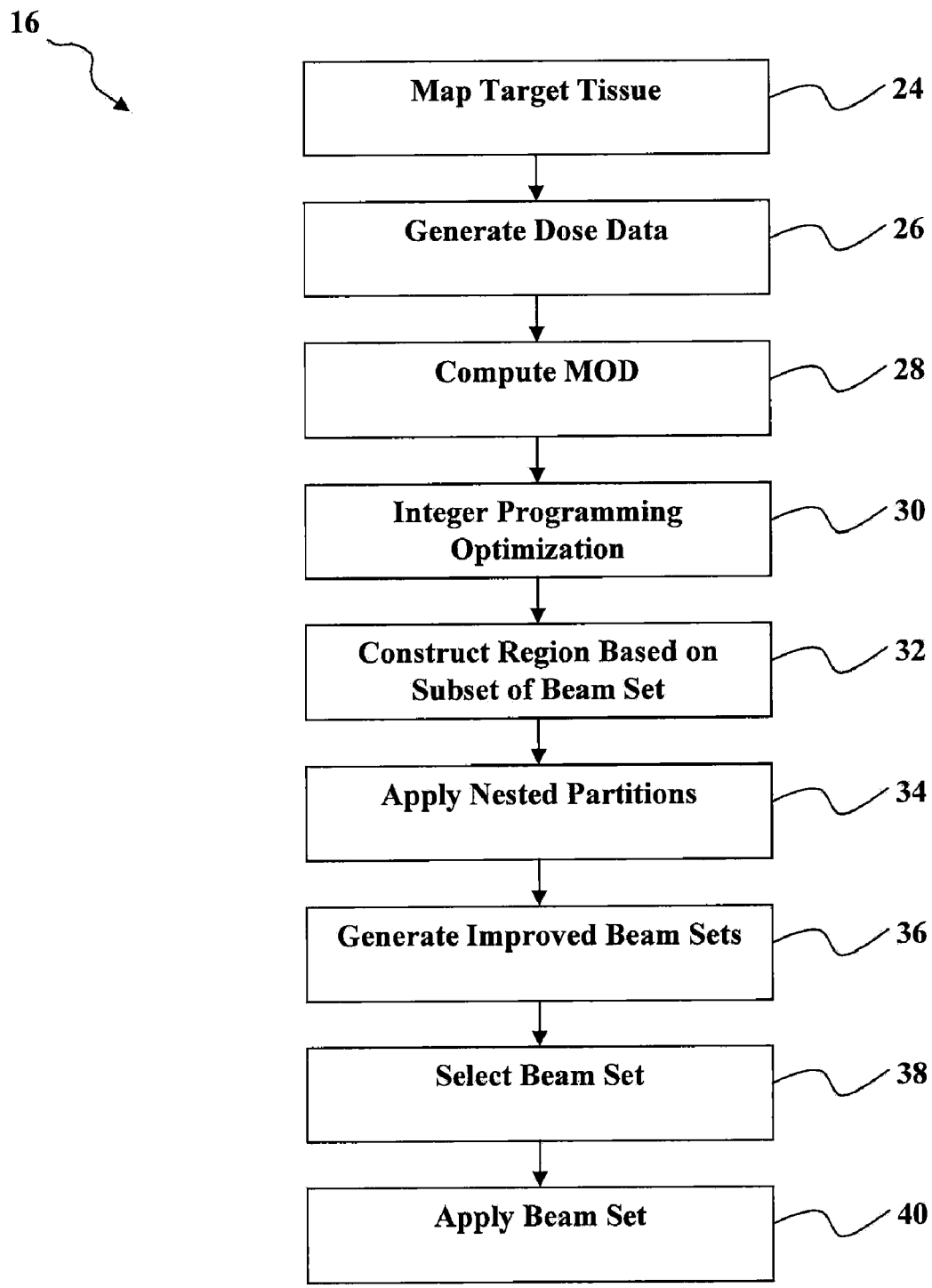
FIG. 2 is a flow chart representing steps for generating a radiation treatment plan in accordance with at least one embodiment of the present invention.

Referring to FIG. 2, in at least one embodiment of the present invention the RTP is generated by first mapping the target tissue at step 24. The input data is generated at step 26, which can include dose data. Input data generation provides tissue distribution data and tissue dose distributions corresponding to beam's-eye-view single-beam plans for 36-360 individual beam angles. Each single-beam plan is normalized so that the average dose for a set of voxels in the planning target volumes (the regions in which the tumor is concentrated), is the same for each plan. The initialization phase utilizes the input data as described above and computes the mean organ doses (MODs) for each organ-at-risk (OAR) specific to each beam angle at step 28. The summary data is imported to an integer-programming (IP) optimization model at step 30. The IP optimization model uses weighted combinations of the MOD data to obtain a quality index for each beam angle. The IP model uses these indices as its objective function and then maximizes this objective subject to a system of constraints that includes spacing, opposition, and cardinality constraints on the beam angles. In order to do this, the problem that is solved and is described below, selects angles to minimize weighted-average OAR impact. One result of this phase is an initial high-quality beam angle set containing the user-specified number of beam angles.

The selection phase utilizes the results of the initialization phase within a nested partitions framework. The nested partitions framework constructs an initial promising region at step 32, which is based on a subset of the initial beam set, and then applies the nested partitions approach at step 34 to seek improved beam sets by using optimization techniques to evaluate each of the beam set samples. The beam set samples can be generated within the nested partitions framework at step 36 through a biased-sampling procedure that takes into account the beam quality indices generated in the initialization phase as well as other information relevant to beam quality. The beam set is selected at step 38 and applied at step 40.

A high-throughput-computing system can be employed to dynamically perform the steps as described above. At least in one embodiment of the invention, computation of data can be accelerated through use of a High-Throughput-Computing (HTC) system that allows parallel computation on networked computers. The data generation processes, and the sample evaluation processes of components are all naturally parallelizable. Alternatively, a variety of other computing environments are contemplated.

Intensity modulated radiation therapy (IMRT) can be used in conjunction with at least one embodiment of the present invention. The IMRT technique enables highly precise external beam radiotherapy treatments for specific types of cancers including prostate cancer, primary brain tumors, metastatic brain tumors, head and neck cancers, and other select cancers. Regarding both 3DCRT and IMRT, the beam angle selection and dose optimization are important to radiation treatment planning.

Beam Angle Selection

In order to obtain an RTP, beam angle selection (BAS) is executed. The quality of a feasible beam set is determined by using properties of the dose delivery that may be achieved using that beam set. Previously, angles were selected manually by treatment planners based on their experience. BAS includes the determination of a plurality of angles selected from 360 or fewer possible delivery angles. In an alternative embodiment, greater than 360 possible delivery angles are available for selection, which can be subject to angle spacing and opposition constraints. However, evaluating every feasible beam set is computationally expensive. By example, 10 angles selected from a possible 360 would generate approximately $8.9 \times 10^{19}$ sets.

Beam angle selection can be performed by an integer-programming (IP) approach that uses Mean Organ-at-risk Dose (MOD) data as input. The same technique of MOD can be used for the warm-start stage of the framework because MOD is straightforward and can be solved quickly relative to using full dose data. Regarding Equation Set 1, let $A=\{0, 1, 2, \ldots, 359\}$ be a candidate collection of angles from which we will select angles, denoted as subset A0 (from the power set of A), to treat the patient. In an alternative embodiment, couch angles can be included in the selection process. The goal of the objective function for BAS is to capture the criteria that a treatment planner, such as a physician or health care worker, uses to decide between good and bad treatment plans, while improving the treatment plan using at least one embodiment of the present invention.

An IP formulation of the BAS problem using only MOD data is possible. The MOD is generated as follows: For each beam orientation, the beam is shaped to the beam's-eye-view projection of the planning target volume (PTV) and a single-beam plan without intensity modulation and without constraints on OAR dose is generated and normalized to yield a mean PTV dose of 2 Gy and the corresponding MOD is calculated. This is done because mean dose is proportional to the integral dose delivered to an organ. Therefore, normalizing each single-beam plan to a mean PTV dose of 2 Gy ensures the same energy deposition in the PTV mass. The formulation in Equation Set 1 illustrates the minimization of the weighted-average OAR impact in the case of selection of n angles from 36 equally-spaced angles.

$$\min \sum_{OAR} \left[ \alpha_{OAR} \left( \sum_{\theta} s_{\theta} MOD_{\theta,OAR} \right) \right]$$

$$s.t. \sum_{\theta} s_{\theta} = n$$

$$s_{\theta} + s_{\theta+\delta} + s_{\theta+2\delta} + \ldots + s_{\theta+(m-1)\delta} \leq 1$$

Equation Set 1

-continued $$\text{for } \theta = 0, 5, 10, \ldots, 355$$

$$s_\theta + s_{\theta+k} \leq 1$$

$$\text{for } k = 180 - \delta, 180.180 + \delta$$

$$\text{and for } \theta \in A' = 0.5, 10, \ldots, 355$$

$$s_\theta \in \{0.1\}$$

The objective function minimizes the weighted MOD over the selected beams. $\alpha_{OAR}$ is the weight associated with an OAR, $\theta$ is the beam-orientation index, so is the binary selection variable for a beam at angle $\theta$. $MOD_{\theta OAR}$ is the MOD for an OAR from a single beam at angle $\theta$, n is the number of beams to be selected, $\delta$ is the spacing between adjacent beams (5°), and m$\delta$ is the minimum geometric spacing required between beams. For example, if 30° is the minimum spacing required between selected beams, then m$\delta$=25° and m=5 in this case. Explained another way, for treatment quality, beams within 25° distance between each other in the full 360° circle are often not selected simultaneously. The first constraint specifies how many angles to select. The inequality constraints specify the minimum spacing between beams and the exclusion of opposed (or nearly opposed) beams. This formulation provides good quality angle sets, and is used for a warm-start nested partitioning for IMRT cases.

Dose Optimization

An additional aspect of radiation treatment planning is dose optimization (DO). This problem includes optimizing beam intensities in 3DCRT or beamlet intensities for 100-200 beamlets used in each beam in IMRT. The number of beamlets can range from 1-1000, and alternatively can be greater than 1000. When performing dose optimization, there are a number of criteria that must be considered, including minimizing the dose delivered to the organ or organs at risk and maximizing the minimum tumor dose. Furthermore, there are constraints defined by dose-volume histograms (DVH), which limit the amount of radiation an organ at risk can receive and identify the minimum amount of radiation the tumor tissue should receive from the dose. For calculation of dose deposition, the patient anatomy is assumed to be segmented into voxels.

Embodiments of the present invention algorithmically combine the BAS and DO problems to simultaneously reach the maximum effectiveness of radiotherapy for each particular patient. However, due to its computational complexity, the maximum effectiveness as provided by the present invention was not previously realized.

Embodiments of the present invention implement a nested partitions (NP) framework to solve the BAS and DO problems together. The nested partitions approach is a powerful optimization algorithm, which can combine adaptive global sampling with a local heuristic search. The nested partition framework uses a flexible partitioning method to divide the search space into regions that can be analyzed individually and then coordinates the results to determine how to continue the search, thereby selectively concentrating the computational effort. The nested partitioning approach can be executed on distributed system environments. By example, a suitable distributed system environment was developed at the University of Wisconsin Madison called Condor (http://www.cs.wisc.edu/condor/).

The nested partition algorithmic approach obtains an optimum result through asymptotic convergence and solves the BAS and DO problems simultaneously. This is achieved by using a dose-averaging approach for the BAS problem and employing the solution as a warm start for NP. Then the angle space is partitioned and sampled based on the initial solution. DO algorithms are incorporated during the evaluation of the quality of a selected angle set. After execution of this method, the set of angles to deliver the radiation were obtained, along with the optimized intensity for each beam in 3DCRT, or intensity maps for each angle in IMRT. At least one embodiment of the present invention provides an automated tool (See FIG. 5) for selecting the radiation delivery angles and improves the dose distribution within patients. The flexibility of the approach allows clinicians to incorporate their knowledge during the solution if this is desired. The computational power of this approach is maximized by utilizing High-Throughput Computing (HTC). By example, the Condor system is an example of a HTC system. The number of beam sets can vary, by example a 7 beam angle set can be selected from a collection of 36-72 angles. The methods described could be scaled to handle all 360 possible angles, although this would require the generation of very large data sets. Additionally, the number of beam angles can be greater or less than 7. Computational results show that this approach provides clinicians a powerful, flexible and efficient method for obtaining high-quality clinical treatment plans.

Nested Partitions Framework

The nested partitions method for coupling dose optimization and beam angle selection maintains a global view of the entire search space, while focusing the search in promising search areas. Commercial treatment planning systems include the Pinnacle[3] system (Phillips Medical Systems, Cleveland, Ohio) and CMS (Elekta Oncology Systems, Crawley, UK The nested partitions method guides the search using a dose optimization algorithm. This methodology allows for continued algorithmic evaluation of dose optimization quality, including a systemic search of beam angle sets.

Figure 3:
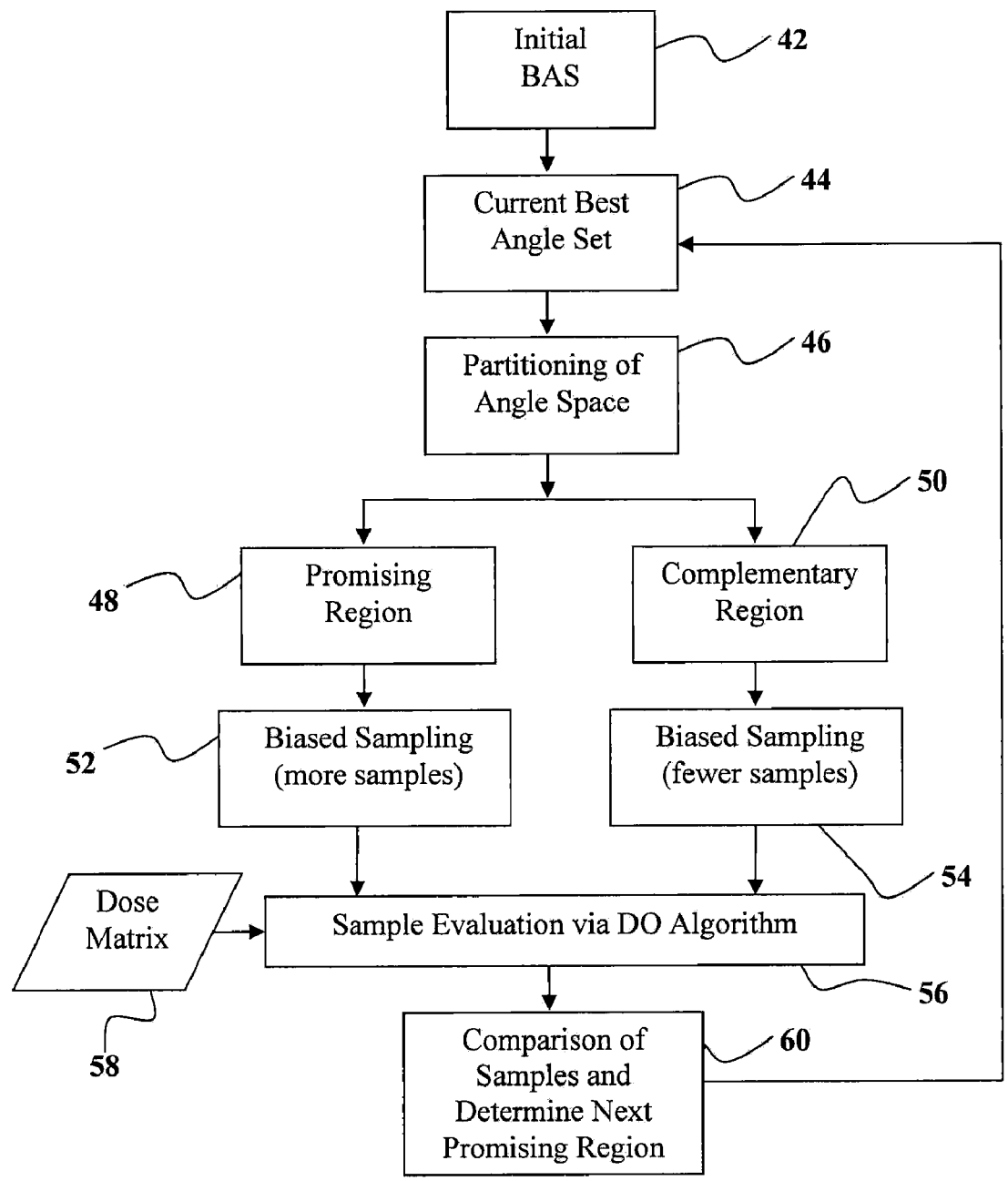
FIG. 3 is a flow chart representing the nested partition framework in accordance with at least one embodiment of the present invention.

Based on the NP framework, beam angle selection and dose optimization are coupled together for radiation treatment planning. There are four steps that are addressed: (1) intelligent partitioning of the solution space; (2) biased sampling methods for obtaining good feasible solutions; (3) applying dose-optimization algorithms to determine the most promising subregion; and (4) backtracking to a complementary region as needed to ensure global convergence. Referring to FIG. 3, one embodiment of the framework is addressed. A fast and simple beam angle selection algorithm can be incorporated to obtain a warm start at step 42. A current best angle set is shown at step 44 and the partitioning of the angle space is provided at step 46. Through each iteration the algorithm constructs a most promising region, based on the current best angle set, which is partitioned into a given number of subregions, and these subregions and the complementary region are sampled. The promising region is generated at step 48 in parallel with the complementary region at step 50. Further biased sampling occurs at steps 52 and 54 based on the promising region and complementary region respectively. To speed up the convergence of the algorithm, biased sampling is used instead of uniform sampling. Then a dose optimization algorithm is applied, at step 56 using a dose matrix 58, to evaluate the samples and the best result (the updated best angle set) is used to determine which region should be the most promising region in the next iteration. Within the NP framework, both beam angle selection and dose optimization engine choices can be very flexible. The samples can also be evaluated at step 56 via commercial treatment-planning software or even based on a clinician's experience (but this could be time-consuming without high throughput computing). The sample evaluation step is well-suited for distributed system environments such as Condor.

Application of the nested partitions framework includes partition of the solution space into several subregions, and in turn partitioning further until each subregion contains only a single solution. Although the nested partition method does not limit the manner of partitioning, the specific strategies employed affect efficiency. Through partitioning, if good solutions are clustered together, the NP algorithm will then quickly identify a set of near-optimal solutions.

In an alternative embodiment, the nested partitions approach adaptively samples from the entire feasible region, or search space, and coordinates the sampling effort with a systematic partitioning of the feasible region. This approach utilizes a flexible partitioning method to divide the search space into regions that can be analyzed individually and then aggregates the results from each region to determine how to continue the search. This type of approach is often referred to as a meta-heuristic. In this particular situation, the meta-heuristic guides the search of a specialized optimization algorithm for radiation treatment planning. As opposed to heuristic approaches, the nested partitions framework provides a global optimum through asymptotic convergence.

Figure 4:
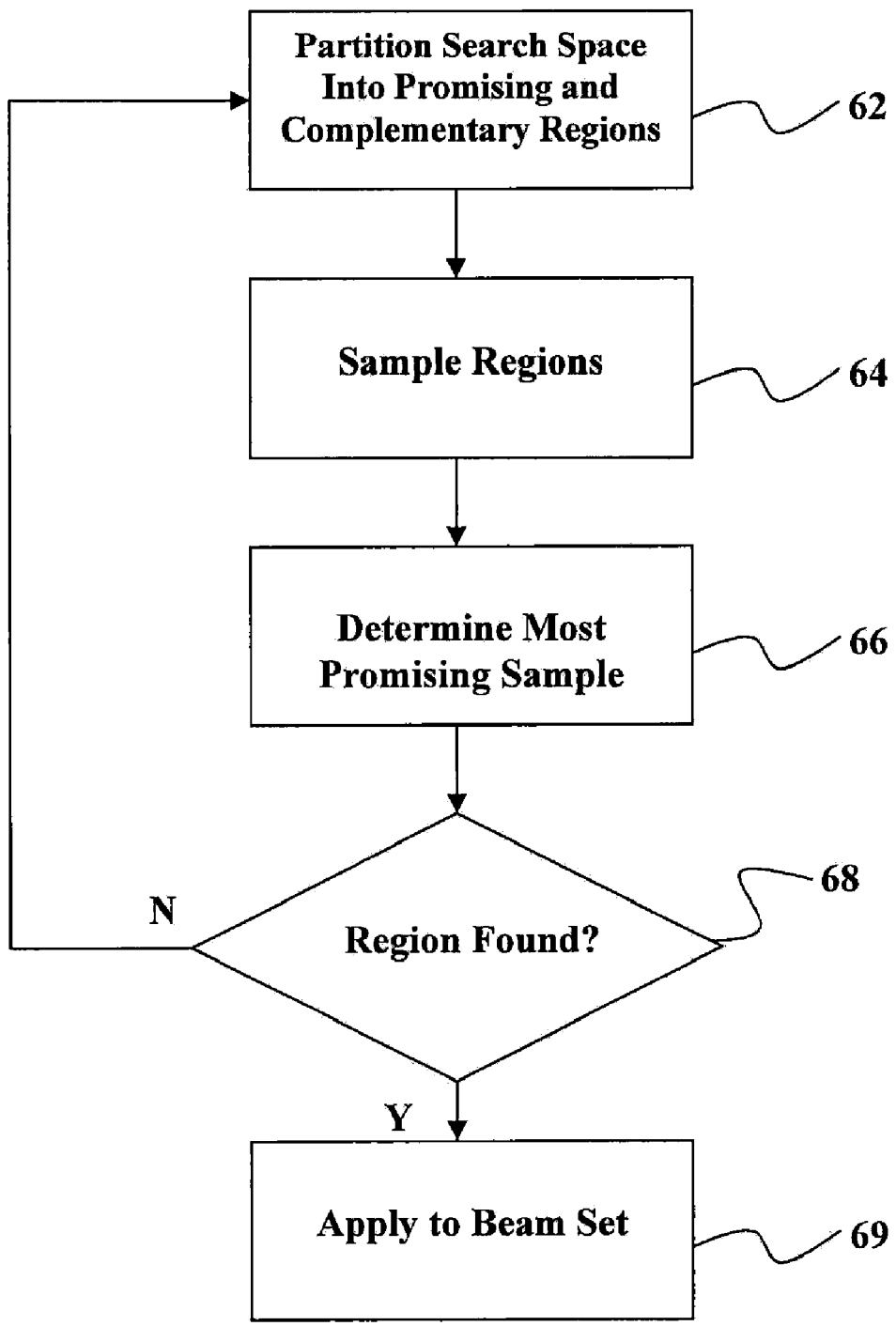
FIG. 4 is flow chart representing steps of the nested partition framework in accordance with at least one embodiment of the present invention.

Referring to FIG. 4, an embodiment of the nested partition framework determines the most promising region, which is considered the sub-region that is most likely to contain the global optimum. The most promising region is partitioned into a plurality of sub-regions at step 62. The sub-regions and remainder of the feasible region (complementary region) are sampled at step 64. The sampling data is used to determine the new most promising region at step 66 for the next iteration. As an iterative process, steps 62, 64, 66 are repeated until the optimum treatment plan is generated. In the event that the best sample resides in the complementary region, then backtracking out of the present iteration occurs at step 68.

By example, the sequence of FIG. 4 was performed for beam angle selection using a Pinnacle$^3$ planning system (Philips Medical Systems, Cleveland, Ohio). The beam's eye view of the planning tumor volume was generated for each of 72 equally-spaced sets. The dose distribution from the conformal beam was calculated and a resulting dose distribution was normalized so that the mean planning tumor volume dose is the daily fraction dose (1.8 Gy in this case). The 72 single-beam plans were generated sequentially through the use of a scripting utility in the Pinnacle$^3$ planning system. Single beam plans can be generated at varying intervals, for example at every 5 degrees. Based upon the single-beam dose distribution, the mean organ-at-risk dose was determined for the organs-at-risk. The generation and calculation of 72-beam plans took approximately 30 minutes on a Sun Blade workstation operating at 2.4 GHz.

Applying the example above with reference to Logical Example 1, the partitioning steps are depicted. A treatment plan can be considered with a number (N) of beam angles such as 7. In alternative embodiments, the beam angles can range from 3 to 10, or greater than 10 beam angles. The solution space, in this example, is divided into 72 sub-regions, which correspond to angles 5 degrees apart. A sub-region selected as a promising region is partitioned further into two sub-regions, one of which is obtained by fixing the second index to be any of the remaining angles. This sequence is repeated until there remains a sub-region with a single solution.

LOGICAL EXAMPLE 1

Generic Partitioning of the Beam Angle Selection Space for 7 Plan Field

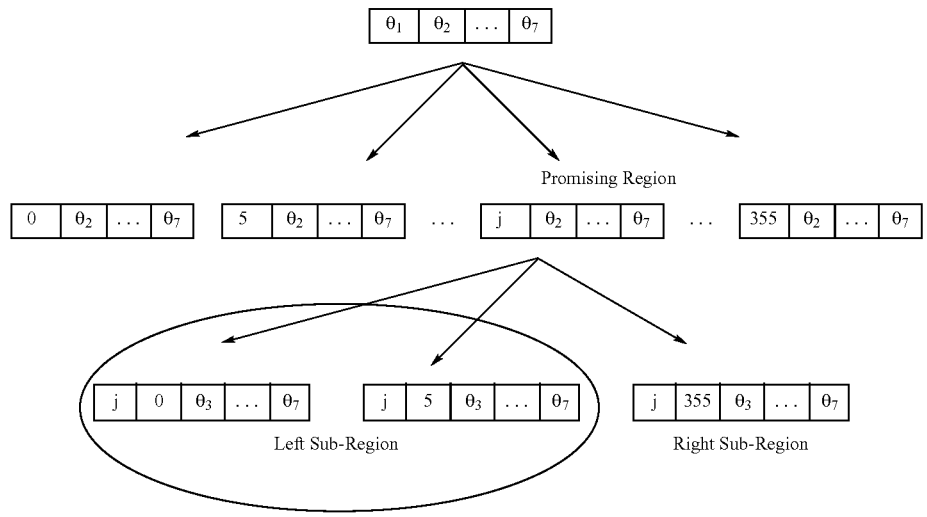

The sampling step 64 of FIG. 4 refers to the generation of the remaining beam angles used to complete the samples in the promising and complementary region after the angle(s) defining the promising region are selected. Incorporation of a simple heuristic algorithm into the sampling scheme improves the sample quality. The present sampling scheme takes into account the beam angle constraints employed in a IP model. The constraints include minimum spacing between adjacent beams and lack of directly opposing beams. Subsequent to the selection of the beam angle for partitioning the solution space, a list of allowable beam angles in each region is defined. Beam angles are chosen sequentially and randomly from a list, such that when an angle is selected the list of allowable angles is redefined.

In order to generate promising regions and complementary regions (Step 66) within the nested partition framework, allowing successive iterations, regions from the previous iteration are ranked based upon a quality index determined by sample evaluations. This index is referred as the promise index. The region having the best promise index determines the next promising region.

If the best sample set is found within the complementary region rather than the promising region, backtracking or "jumping out" of the promising region can occur. The present embodiment includes two approaches for backtracking: (1) the regions that lead from the current most promising region back to the entire feasible region are recorded, and can be used for backtracking; and (2) it is possible to move out of the current promising region to a set related to the complementary region. The first approach provides for a slight change in the sample distribution at each iteration and the second approach permits drastic changes. In an alternative embodiment other approached would be implemented for backtracking.

Results of the nested partition methodology for two sample cases are summarized below after a brief description of the cases. Each case was benchmarked against different beam angle selection methods, which include Equi-spaced (EQ), integer programming method (IP) and greedy approach (GR) methods. The nested partitions approach included two different embodiments, frequency-based partitioning ($NP_f$) and weight-based partitioning ($NP_w$).

Test Case 1

Feasibility of the nested partition approach to generating a radiation treatment plan was tested using a head and neck case. Test case 1 involved concave targets with organs at risk located in close proximity to the target tumor tissue. The target tumor volume for test case 1 consisted of 169.2 cc. The prescription dose was 50.4 Gy, which was delivered in 1.8 Gy fractions. The organ at risk constraints were as follows: ≦33% of the parotids were allowed to receive 26 Gy or more and the maximum cord dose was 39 Gy. Plans were normalized so that at least 90% of the target tumor volume received the prescription dose.

Test Case 2

Feasibility of the nested partition approach to generating a radiation treatment plan was tested using a pelvic case. Test case 2 involved concave targets with organs at risk located in close proximity to the target tumor tissue. The target tumor volume for test case 3 consisted of 733.0 cc. The prescription dose was 45.0 Gy, which was delivered in 1.8 Gy fractions. The organ at risk constraints were as follows: ≦35% of the rectum and bladder were allowed to receive 30 Gy or more and ≦25% of the bowel was allowed to receive 25 Gy or more. Plans were normalized so that at least 90% of the target tumor volume received the prescription dose.

TABLE 2

Test Case 2 Pelvic

| Beam angle selection method | % volume of PTV receiving at least 115% of prescription dose | % volume of rectum receiving at least 30 Gy | % volume of bladder receiving at least 26 Gy | % volume of bowel receiving at least 39 Gy |
|---|---|---|---|---|
| EQ | 42.8 | 64.0 | 68.7 | 54.2 |
| IP | 61.2 | 70.1 | 65.1 | 54.4 |
| GR | 57.7 | 72.8 | 69.9 | 48.1 |
| $NP_f$ | 34.2 | 55.9 | 59.2 | 52.3 |
| $NP_w$ | 46.5 | 54.4 | 65.1 | 49.3 |

A further comparison of NP with some alternative approaches is provided in Table 3. The promise index provides a means for comparing the different algorithmic approaches. The nested partition framework provided superior results as compared to the equi-spaced, integer programming model and greedy approach. The nested partition approach resulted in the lowest achieved dose-volume values at the levels at which constraints were imposed for the left parotid and the cord with the frequency-based partitioning approach generally outperforming the weight-based partitioning approach for this case. The nested partitioning frequency based approach resulted in the lowest volume of the target tumor volume receiving 110% of the prescription dose. These improvements are reflected in the promise index, which provides a composite score for the treatment.

TABLE 1

Test Case 1 Head and Neck

| Beam angle selection method | % volume of PTV receiving at least 110% of prescription dose | % volume of left parotid receiving at least 26 Gy | % volume of right parotid receiving at least 26 Gy | % volume of cord receiving at least 39 Gy | Maximum cord dose (Gy) |
|---|---|---|---|---|---|
| EQ | 16.4 | 74.1 | 35.3 | 3.4 | 41.0 |
| IP | 17.8 | 76.7 | 40.8 | 31.7 | 42.5 |
| GR | 57.2 | 49.5 | 41.4 | 27.3 | 48.0 |
| $NP_f$ | 17.6 | 44.0 | 48.3 | 1.4 | 43.0 |
| $NP_w$ | 3.5 | 47.4 | 44.9 | 1.0 | 40.5 |

TABLE 3

Table Promise index resulting from the 5 methods considered for the head and neck and whole pelvis cases. EQ = equi-spaced, IP = integer programming model, GR = greedy approach, $NP_f$ = nested partitions (frequency-based partitioning), $NP_w$ = nested partitions (weight-based partitioning)
Promise index

| Beam Angle Selection Method | Head and neck case | Whole pelvis case |
| --- | --- | --- |
| EQ | 1.413 | 4.488 |
| IP | 2.574 | 4.522 |
| GR | 1.631 | 4.932 |
| $NP_f$ | 0.840 | 3.670 |
| $NP_w$ | 0.822 | 3.433 |

Figure 5:
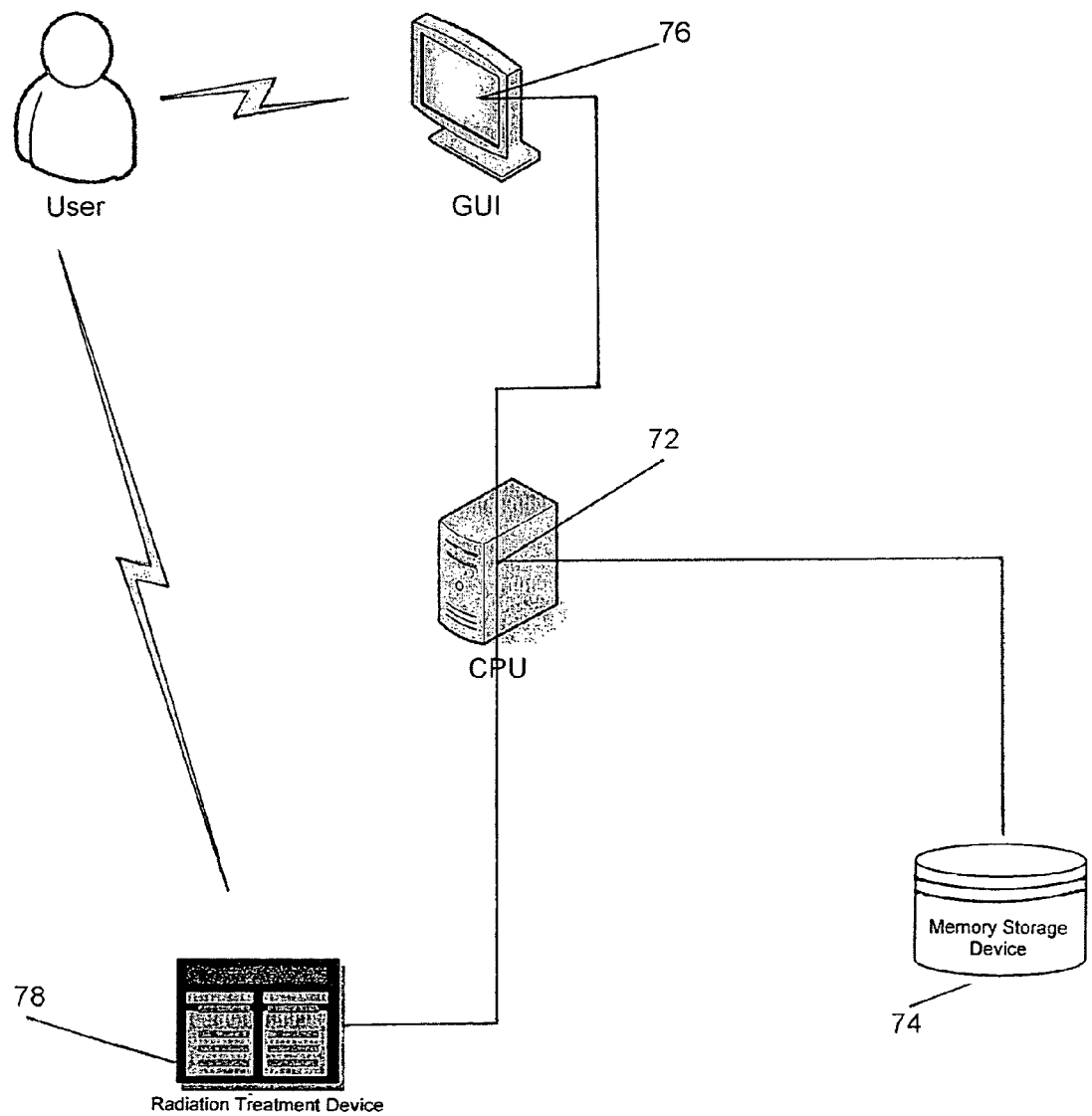
FIG. 5 is a block diagram representing a radiation treatment planning system in accordance with at least one embodiment of the present invention.

Referring to FIG. 5, a treatment planning system 70 is shown. The treatment planning system includes a central processing unit (CPU) 72 operatively connected to a memory storage device 74, a graphical user interface 76, and a radiation treatment device 78. The radiation treatment device 78 can implement 3DCRT. In an alternative embodiment, the radiation treatment device implements IMRT. At least one embodiment of the nested partitions approach to radiation treatment planning is implemented by system 70. The CPU 72 can be a desktop computer, a high throughput computing system, or an alternative suitably equipped computer system. A system 70 user can be a health care provider interfacing with the GUI or a patient being treated by the device 78.

Embodiments of the present invention provide a novel beam angle selection algorithm that can be implemented with a commercial treatment planning system to benchmark its performance against potential other beam angle selection approaches. It is often the case that combinatorial optimization problems, especially those on a large scale, are notoriously difficult to solve to optimality, because verification of optimality cannot be established by "local properties" associated with a proposed optimal solution. The nested partition approach generates a large number of feasible solutions spread across the entire solution space, thereby providing confidence that further computation is highly unlikely to produce significant improvements in the solution obtained. The integer programming model was established as a good "warm start", but the nested partition approach was able to improve upon the results with significant improvement. This level of improvement translates into more effective delivery of radiation therapy to patients, which in turn provides for safer and more successful radiation treatment. IMRT treatment plans can be optimized through the nested partition framework, which enabled reduced dose delivery to organs at risk in the test cases. Furthermore, the nested partition approach has versatility by allowing the dose calculation algorithm of commercial planning systems to be embedded within the nested partition framework.

It is specifically intended that the present invention not be limited to the embodiments and illustrations contained herein, but include modified forms of those embodiments including portions of the embodiments and combinations of elements of different embodiments as come within the scope of the following claims.

The invention claimed is:

1. A medical treatment planning system comprising:
a central processing unit (CPU) for performing computer executable instructions; and
a memory storage device storing computer executable instructions that when executed by the CPU cause the CPU to perform a process for generating a radiation treatment plan based in-part on a nested partition framework.

2. The system according to claim 1, wherein the nested partition framework is configured to couple beam angle selection and dose optimization data associated with a patient.

3. The system according to claim 2, wherein the beam angle selection includes a range of beam angles from about 1 beam angle to about 360 beam angles.

4. The system according to claim 1, wherein the radiation treatment plan is configured for maximizing delivery of a radiation dose to a target tissue and minimizing radiation delivery to a healthy tissue adjacent the target tissue.

5. The system according to claim 1, wherein the treatment plan is configured for use with intensity modulated radiation therapy (IMRT).

6. The system according to claim 1, wherein the treatment plan is configured for use with three dimensional conformal radiation therapy (3D CRT).

7. The system according to claim 1, wherein the radiation treatment plan is configured for the treatment of a patient's cancer.

8. A method of preparing a patient treatment plan comprising:
obtaining medical patient imaging data;
identifying a target tissue within a patient based in part on the imaging data; and
generating a treatment plan based in-part on a nested partition framework, the imaging data being used within the nested partition framework.

9. The method according to claim 8, further comprising: obtaining patient specific dose data, wherein the dose data is used within the nested partition framework.

10. The method according to claim 8, wherein the generating includes coupling of beam angle selection and dose optimization.

11. The method according to claim 10, wherein the imaging data includes tissue distribution data that is a plurality of tissue dose distributions corresponding to beam's-eye-view single beam plans for a plurality of beam angles.

12. The method according to claim 10, wherein an integer programming optimization model utilizes weighted combinations of mean organ dose data to generate a quality index for each beam angle.

13. The method according to claim 10, wherein the nested partition framework constructs an initial promising region based upon a warm-start and subsequently applies a nested partition global viewpoint to seek improved beam sets.

14. The method according to claim 10, wherein a high throughput computing system is employed for at least one of the steps, the high throughput computing system performing at least two steps in parallel.

15. The method according to claim 10, wherein each single-beam plan is normalized, an average dose to a set of voxels in planning target volumes is the same for each plan.

16. The method according to claim 10, wherein the beam angle selection includes a plurality of beam angles in a range from about 3 beam angles to about 10 beam angles.

17. The method according to claim 8, wherein the treatment plan is prepared for intensity modulated radiation therapy (IMRT).

18. The method according to claim 8, wherein the treatment plan is prepared for three dimensional conformal radiation therapy (3D CRT).

19. The method according to claim 8, wherein dose data includes dose distributions corresponding to beam's eye view single beam treatment plans.

20. The method according to claim 8, wherein the nested partition framework uses biased sampling to improve sample quality.

21. The method according to claim 8, wherein the nested partition framework uses biased variables to improve the partitioning process.

22. The method according to claim 8, wherein the nested partition framework uses a scoring method to evaluate sample quality.

23. A medical treatment planning system comprising:
   a processor for performing computer executable instructions; and
   a memory device storing computer executable instructions that when executed by the processor cause the processor to perform a process for generating a radiation treatment plan, the process performing an algorithmic coupling of beam angle selection and dose optimization within a nested partition framework.

24. The system according to claim 23, wherein the processor is a high throughput computing system.

25. The system according to claim 24, wherein the high throughput computing system is connected to a radiation treatment device.

26. The system according to claim 25, wherein the radiation treatment device is configured for intensity modulated radiation treatment (IMRT).

* * * * *

UNITED STATES PATENT AND TRADEMARK OFFICE
CERTIFICATE OF CORRECTION

PATENT NO. : 7,876,882 B2  
APPLICATION NO. : 12/025588  
DATED : January 25, 2011  
INVENTOR(S) : Robert R. Meyer, Leyuan Shi and Warren D. D'Souza Page 1 of 1

It is certified that error appears in the above-identified patent and that said Letters Patent is hereby corrected as shown below:

Column 1, line 15, delete "The invention was made with United States Government support awarded by the following agency: National Science Foundation (NSF) under Grant #DMI-0400294 and Grant #03-65557."

Insert --This invention was made with government support under 0400294 awarded by National Science Foundation. The government has certain rights in the invention.--

Column 1, line 18, insert --FIELD OF THE INVENTION-- directly above the paragraph beginning on line 19.

Signed and Sealed this
Twenty-sixth Day of April, 2011

David J. Kappos
*Director of the United States Patent and Trademark Office*